US008455508B2

(12) United States Patent
Luangdilok et al.

(10) Patent No.: US 8,455,508 B2
(45) Date of Patent: Jun. 4, 2013

(54) SUSTAINED RELEASE PARENTERAL FORMULATIONS OF BUPRENORPHINE

(75) Inventors: Carmela Luangdilok, Westmont, IL (US); Douglas R. Flanagan, Iowa City, IA (US); Luk-Chiu Li, Lake Forest, IL (US); Matthew Widman, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 174 days.

(21) Appl. No.: 12/636,227

(22) Filed: Dec. 11, 2009

(65) Prior Publication Data
US 2010/0093778 A1 Apr. 15, 2010

Related U.S. Application Data

(63) Continuation of application No. 12/038,890, filed on Feb. 28, 2008, now abandoned.

(60) Provisional application No. 60/892,077, filed on Feb. 28, 2007.

(51) Int. Cl.
A01N 43/42 (2006.01)
A61K 31/44 (2006.01)

(52) U.S. Cl.
USPC .......................................................... 514/279

(58) Field of Classification Search
USPC .......................................................... 514/279
See application file for complete search history.

(56) References Cited

U.S. PATENT DOCUMENTS

| 4,613,505 | A | | 9/1986 | Mizushima et al. |
| 5,075,341 | A | | 12/1991 | Mendelson et al. |
| 5,229,130 | A | | 7/1993 | Sharma et al. |
| 5,346,903 | A | | 9/1994 | Ackerman et al. |
| 5,731,355 | A | * | 3/1998 | Jones et al. ............... 514/731 |
| 5,965,160 | A | | 10/1999 | Benita et al. |
| 6,140,373 | A | | 10/2000 | May et al. |
| 6,153,225 | A | | 11/2000 | Lee et al. |
| 6,174,540 | B1 | | 1/2001 | Williams et al. |
| 6,197,344 | B1 | | 3/2001 | Chang et al. |
| 6,228,398 | B1 | | 5/2001 | Devane et al. |
| 6,335,035 | B1 | | 1/2002 | Drizen et al. |
| 6,495,155 | B1 | | 12/2002 | Tice et al. |
| 6,623,762 | B2 | | 9/2003 | Roser et al. |
| 6,667,048 | B1 | | 12/2003 | Lambert et al. |
| 6,680,067 | B2 | | 1/2004 | Hu et al. |
| 7,276,250 | B2 | | 10/2007 | Baichwal et al. |
| 2002/0119916 | A1 | | 8/2002 | Hassan |
| 2002/0155129 | A1 | | 10/2002 | Roser |
| 2003/0055075 | A1 | | 3/2003 | Rubsamen |
| 2003/0073665 | A1 | * | 4/2003 | Thompson et al. ............... 514/58 |
| 2003/0113372 | A1 | | 6/2003 | Hu et al. |
| 2004/0142013 | A1 | | 7/2004 | Rubsamen |
| 2005/0069591 | A1 | | 3/2005 | Bernstein et al. |

FOREIGN PATENT DOCUMENTS

| CN | 1478465 | 3/2004 |
| CN | 1533764 | 10/2004 |
| EP | 0368409 | 11/1989 |
| EP | 1142567 | 12/1996 |
| EP | 1140018 | 12/1999 |
| JP | 2000212067 | 8/2000 |
| JP | 2004175706 | 6/2004 |
| JP | 3701693 | 7/2005 |
| WO | 8809676 | 12/1988 |
| WO | 0021505 | 4/2000 |
| WO | 0115699 | 3/2001 |
| WO | 2007103185 | 9/2007 |

OTHER PUBLICATIONS

JP07-196510, Machine translation.*
Jacques "Optical properties of "Intralipid", an aqueous suspension of lipid droplet", by Stephen Jacques, Oregon Medical laser center, Apr. 1, 1998.*
Heel, et al., Drugs, "Buprenorphine: A Review of its Pharmacological Properties and Therapeutic Efficacy", 17: 81-110 (1979).
Robinson, S., CNS Drugs, Rev., "Buprenorphine: A Analgesic with an Expanding Role in the Treatment of Opioid Addiction", 8(4): 377-390 (2000).
Hoskin, et al., Drugs, "Opioid Agonist-Antagonist Drugs in Acute and Chronic Pain States", 41(3): 326-344 (1991).
Tzschentke, T., Psychopharmacology, Behavioral Pharmacology of buprenorphine, with a Focus on Preclinical Models of Rewards and Addiction, 161: 1-16 (2002).
Sittl, R., Clin. Ther., "Analgesic Efficacy and Tolerability of Transdermal Buprenorphine in Patents with Inadequately Controlled Chronic Pain Related to Cancer and other Disorders: A Multicenter, Randomized, Double-Blind, Placebo-Controlled Trial", 25: 150-168 (2003).
Sittl. R., Expert Rev. Neurother., "Transdermal Buprenorphine in the Treatment of Chronic Pain", (3): 315-323 (2005).
Sobel, et al., Drug and Alcohol Dependence, "Open-label Trial of an Injection Depot Formulation of Buprenorphine in Opioid Detoxification", 73: 11-22 (2004).
Liu, et al., J. Chromatogr. B, "Simultaneous Determination of Buprenorphine and its Prodrug, Buprenorphine Propionate, by High-performance Liquid Chromatography with Fluorescence Detection: Application to Pharmacokinetic Studies in Rabbits". 818: 233-239 (2005).

(Continued)

Primary Examiner — Brandon Fetterolf
Assistant Examiner — Jean Cornet
(74) Attorney, Agent, or Firm — Lisa V. Mueller; Michael Best & Friedrich LLP

(57) ABSTRACT

An oil-in-water buprenorphine formulation including buprenorphine and a surfactant that emulsifies the buprenorphine in oil, wherein the drug release is controlled by varying the oil concentration and/or pH. A buprenorphine aqueous suspension formulation including a free base buprenorphine and a suspension stabilizer. A buprenorphine oil formulation including a buprenorphine salt suspended in a pharmaceutically acceptable oil. Methods of providing sustained release of buprenorphine over a period of time.

10 Claims, 2 Drawing Sheets

OTHER PUBLICATIONS

Liu, et al., Anesth. Anal., "Novel Depots of Buprenorphine Prodrugs Have a Long-Acting Antinociceptive Effect", 102: 1445-1451 (2006).

Collier, et al., Nature, "Modification of Morphine Withdrawal by Drugs interacting with Humoral Mechanisms: Some Contradictions and their Interpretation", 237: 220-223 (1972).

Salem, A., et al., Journal of Pharm. and Tox. Methods, "Absorption of Morphine from a Slow-Release Emulsion Used to Induce Morphine Dependence in Rats", 40: 159-164 (1998).

Larsen. D., et al., J. of Controlled Release. "In Vivo Release of Piperocaine from Subcutaneously Administered Oily Solution. Comparison with In Vitro Release", 81: 145-154 (2002).

International Search Report, PCT Application No. PCT/US1008/055211, mailing date Jul. 29, 2008.

Data Base WPI Week 199539, Thomson Scientific, London, GB; AN 1995-299497, XP-002487837 (JP07196510, Aug. 1, 1995).

* cited by examiner

SUSTAINED RELEASE PARENTERAL FORMULATIONS OF BUPRENORPHINE

CROSS REFERENCE SECTION TO RELATED APPLICATIONS

This application is a continuation of U.S. patent application Ser. No. 12/038,890, filed Feb. 28, 2008, which claims priority to U.S. Provisional Application Ser. No. 60/892,077, filed Feb. 28, 2007, all of which are incorporated herein by reference.

FIELD OF INVENTION

The present invention relates to sustained release pharmaceutical composition formulations and related methods. More specifically, the present invention is directed towards sustained release injectable formulations of buprenorphine.

BACKGROUND ART

Buprenorphine is a semi-synthetic opioid analgesic with mixed agonist-antagonist properties. Besides being 20-40 times more potent than morphine, one of its main advantages is that the dose does not need to be increased during chronic administration. Buprenorphine can be in various forms such as sublingual tablets (0.2 mg) for the treatment of moderate, severe acute, and chronic pain, or as a pre-operative medication. Sublingual tablets containing 0.4, 2 and 8 mg of the drug are used for the treatment of opioid addiction. Alternatively, it is available as an injection (0.3 mg/mL) for intravenous (hereinafter, "IV"), intramuscular (hereinafter, "IM"), intrathecal, and epidural administration as an analgesia in cases of severe acute pain and as a pre-medication. Recommended doses are 200-600 µg by IV or IM injection every six to eight hours, 30-45 µg intrathecally or 100-300 µg epidurally every six to twelve hours or 400 µg sublingually every six to eight hours (R. C. Heel, R. N. Brogden, T. M. Speight and G. S. Avery, Drugs 17 (1979) 81-110; S. E. Robinson, CNS Drug Rev. 8 (2000) 377; P. J. Hoskin, G. W. Hanks, Drugs 30 (1991) 326; T. M. Tzschentke, Psychopharmacology 161 (2002) 1).

The prior art includes various references disclosing injectable slow-release formulations. For example, U.S. Pat. No. 6,495,155 discloses an injectable slow-release partial opioid agonist and/or opioid antagonist formulation in a poly (D, L-lactide) excipient with a small amount of residual ethyl acetate. The microparticles are under 125 µm in diameter and can be readily injected intramuscularly to provide at least about 0.5 ng/ml of drug over an extended period of time (28-60 days). The formulations are provided for use in the treatment of alcoholics and heroin addicts. Additionally, a subcutaneous depot product (Norvex™) exists wherein buprenorphine microcapsules consisting of buprenorphine base and biodegradable PLA-PGA polymer are disclosed (B. -F. X. Sobel et al. Drug and Alcohol Dependence 73 (2004) 11). Moreover, there are buprenorphine transdermal delivery systems (TDS) (e.g., Transtec™), formulated as a matrix patch and licensed for the treatment of moderate to severe cancer pain and severe pain not responding to non-opioid analgesics. The patch is available in three strengths delivering 35, 52.5 or 70 mcg/hr over seventy-two hours (R. Sittl et al., Clin. Ther. 2003 January; 25(1): 150; Expert Rev. Neurother. 2005 May; 5(3): 315).

A study has found that buprenorphine propionate when prepared as a depot had a long-lasting analgesic effect, which was 7.5-fold longer than the traditional dosage form of buprenorphine in saline preparation, following IM injection in rats. The long lasting effect of IM depot of buprenorphine propionate is reported to be due to a slow release of buprenorphine propionate from its oil vehicle (S. -Y. Liu et al., J. Chromatogr B 818 (2005) 233; J. J. Wang, Patent of the Republic of China, No. 1226830 (2005)). They have subsequently synthesized and formulated other depots of buprenorphine esters, buprenorphine enanthate and decanoate. The buprenorphine decanoate in oil produced a 14-fold longer duration of action than buprenorphine HCl in saline (K. -S. Liu et. al. Anesth Analg 2006; 102; 1445).

U.S. Pat. No. 6,335,035 discloses the preparation of a sustained release delivery system using a polymer matrix containing a drug for use in treating acute or chronic conditions. The drug is dispersed within a polymer matrix solubilized or suspended in a polymer matrix. The polymer matrix is composed of a highly negative charged polymer material such as polysulfated glucosoglycans, glycosaminoglycans, mucopolysaccharides and mixtures thereof, and a nonionic polymer such as carboxymethylcellulose sodium, hydroxyethyl cellulose, hydroxypropyl cellulose, and mixtures thereof.

U.S. Pat. No. 4,613,505 discloses a fat emulsion specific to an ester of flurbiprofen to provide an orally and parenterally administrable, particularly intravenously administrable, preparation having an excellent anti-inflammatory, analgesic and antipyretic activity and only a minor side effect.

U.S. Pat. No. 6,197,344 discloses controlled release suspension formulations of the opioid analgesic, butorphanol and the use of such formulations for pain management over periods of time ranging from 12 to 24 hours. South African Patent Application 91/4549 is referenced, which discloses microsphere pharmaceutical formulations and the use of such in delivering therapeutic agents. Pharmaceutically active substances that can be administered using such microspheres are tranquilizers, anti-emetics, vasodilators, antihistaminics, steroids and analgesics.

Finally, slow release emulsions containing either morphine base or morphine hydrochloride were prepared and formulated by Collier et. al. The preparation consists of suspending 150 mg of morphine base in 0.75 mL of an emulsifying agent, mannide monooleate ("Aracel A"), and 4.25 mL of light liquid paraffin. This oily phase was emulsified with 5 mL of 0.9% w/v NaCl in water (H. O. J. Collier et. al., Nature Vol 237 May 26, 1972).

Although the use of emulsions and suspensions for drug delivery is not uncommon and has been used in other analgesics, there are also problems associated with them. However, sustained release injectable buprenorphine formulations that exist in the prior art utilize more complicated systems such as microparticles or prodrugs in an oil vehicle. More particularly, the manufacturing of microparticles involves utilizing complex and costly processes with the use of organic solvents. Additionally, it can be difficult to achieve sterility of microparticles and other oil solutions because terminal sterilization is not always possible. In addition to these disadvantages, it is difficult to appropriately control the release of a drug such as buprenorphine in an injectable dosage form in order to achieve the desired onset and duration of analgesic effects in the target species. Accordingly, there continues to be a need for reasonably simpler and more practical formulations for sustained release of buprenorphine.

SUMMARY OF THE INVENTION

The present invention provides, in one embodiment, an oil-in-water buprenorphine formulation including buprenorphine and a surfactant that emulsifies the buprenorphine in oil, wherein the buprenorphine release is controlled by varying the oil concentration and/or pH of the emulsion. Additionally, the present invention provides an aqueous suspension formulation including free base buprenorphine and a suspension stabilizer. Further, the present invention provides an oil formulation including buprenorphine salt suspended in a pharmaceutically acceptable oil. The present invention also provides various methods of controlling the release of buprenorphine over a period of time through administration of the various formulations. In addition, the present invention provides methods of manufacturing the various formulations thereof.

DESCRIPTION OF DRAWINGS

Other advantages of the present invention will be readily appreciated, as the same becomes better understood by reference to the following detailed description when considered in connection with the accompanying drawings, wherein.

DETAILED DESCRIPTION OF THE INVENTION

Figure 1:
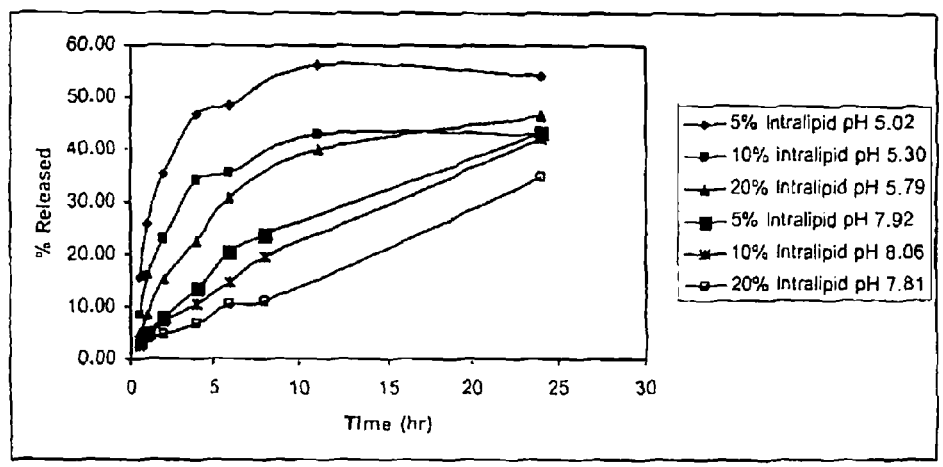
FIG. 1 is a chart demonstrating a buprenorphine release profile from Intralipid emulsions into NS.

Generally, the present invention is directed towards formulations and related methods of preparation and manufacturing of a sustained release injectable formulation of buprenorphine. More specifically, the formulation can be an oil-in-water emulsion, an aqueous suspension of the buprenorphine free base, or an oil suspension of the buprenorphine salt, wherein any of the formulations can include or exclude a preservative. The present invention also relates to the use of such formulation for controlled release of buprenorphine over a period of twelve to forty-eight hours for human or veterinary medicine.

The present invention provides numerous advantages over the prior art. The present invention provides a simpler, more practical, and inexpensive method of preparing formulations that can achieve sustained release of buprenorphine. The present invention provides flexibility in controlling the release of buprenorphine by varying the different factors that control the release. These factors include, but are not limited to, lipid concentration, pH, particle or globule size, and buprenorphine concentration. Further, extensive data and excellent tissue biocompatibility have been demonstrated for emulsions as a drug delivery system. The administration of an emulsion subcutaneously or intramuscularly is straightforward without the need for reconstitution as with microparticles. Owing to the relatively low viscosity of an emulsion, the use of smaller needle size is more feasible with an emulsion than an oil solution.

As an application, for example, in the horse, the onset of action is approximately fifteen minutes after IV dosing of buprenorphine. The peak effect occurs in thirty to forty minutes and the duration of action can last up to eight hours. The disposition of buprenorphine (10 μg/kg) after intravenous and intramuscular as well as oral mucosal route has been reported in cats. Based on changes in thermal threshold, i.m. doses of 10 μg/kg resulted in a slow onset (two hours) of analgesia, but once established, this lasted at least six hours. Use of the sustained release formulation could prolong the duration of action (12 to 48 hours) in these species.

As used herein, the term "buprenorphine" means an opioid drug with partial agonist and antagonist actions. It can be in various forms including, but not limited to, a free base form or as a salt. The salt form can be buprenorphine HCl or any other similar salts known to those of skill in the art.

The present invention has numerous embodiments. One embodiment of the present invention is an oil-in-water buprenorphine formulation including buprenorphine and a surfactant that emulsifies the buprenorphine in oil, wherein the release is controlled by varying the oil concentration and/or pH. The buprenorphine can be a free base or a salt. Further, the surfactant can be, but is not limited to, synthetic non-ionic surfactants, polypropylene polyethylene block copolymers, phosphatides, egg phosphatide, combinations thereof, and any other similar surfactants known to those of skill in the art. In this embodiment, the buprenorphine can be dissolved in a water immiscible solvent including, but not limited to, vegetable oil, soybean oil, safflower oil, cottonseed oil, corn oil, sunflower oil, arachis oil, castor oil, olive oil, ester of a medium or long chain fatty acid such as a mono-, di-, or triglyceride, ethyl oleate, isopropyl myristate, polyoxyl hydrogenated castor oil, combinations thereof, and other similar solvents known to those of skill in the art. Moreover, the formulation can optionally include glycerol, which can cause the formulation to be isotonic. The composition can also include, but is not limited to, pH adjusting agents including, but not limited to, sodium hydroxide, and a pharmaceutically acceptable buffer system such as, but not limited to, sodium citrate and sodium phosphate. Preferably, the pH is adjusted to be between about 6 to about 9. Further, the formulation can include a preservative such as, but not limited to, benzyl alcohol, EDTA, combinations thereof, and any other similar preservative known to those of skill in the art. Finally, the remaining formulation is water.

Another embodiment is directed towards a buprenorphine aqueous formulation where the free base buprenorphine is suspended in an aqueous medium. In this embodiment, the free base buprenorphine can be formed by the addition of an alkali metal salt such as, but not limited to, NaOH to a buprenorphine salt solution. Further, a suspending agent can be added, but is not limited to, polyvinyl pyrrolidone (PVP), sodium carboxymethylcellulose (Na— CMC), dextran, and other similar agents known to those of skill in the art. Alternatively, the aqueous suspension can be formulated by dispersing the buprenorphine free base into the suspending agent solution and mixing with a high shear homogenizer. Buprenorphine has a pKa of about 8.24. The solubility of the buprenorphine is inversely proportional to pH over the pH range of about 6.0 to 8.0 and this can be utilized to control the release. The initial rate of release of the drug is higher at low pH levels. The composition can further include a surfactant such as, but not limited to, Pluronic F127, polysorbates and other surfactants acceptable for parenteral administration. Additionally, the formulation can include additional substances such as a buffer including, but not limited to, sodium citrate and sodium phosphate, and other similar buffers known to those of skill in the art. Further, the formulation can include a preservative such as, but not limited to, benzyl alcohol, methyl paraben, propyl paraben, combinations thereof, and any other similar preservative known to those of skill in the art.

A further embodiment is directed towards a buprenorphine oil formulation where a buprenorphine salt is suspended in a pharmaceutically acceptable oil. The buprenorphine salt can be, but is not limited to, buprenorphine HCl. Further, the pharmaceutically acceptable oil includes, but is not limited to, cottonseed oil, corn oil, peanut oil, soybean oil, combinations thereof, and other similar oils known to those of skill in the art. The composition can further include a suspending agent such as a sorbitan fatty acid hexitan ester.

The present invention also provides methods of providing sustained release of buprenorphine over a period of time by administering any of the formulations of the present invention.

The above discussion provides a factual basis for the use of the present invention described herein. The present invention is further illustrated by the following non-limiting examples.

EXAMPLES

Example One Preparation of Buprenorphine Formulations

Preparation of 1.5 Mg/Ml Buprenorphine in 30% Intralipid® Oil-in-Water Emulsion at pH 8.0

7.5 mg (free base equivalent) of buprenorphine HCl was dissolved in ethanol and sterile filtered into a vial. The ethanol was evaporated by purging with nitrogen. 4.7 mL of 30% Intralipid® fat IV emulsion was added into the vial containing the sterile buprenorphine HCl. The vial was shaken vigorously for about thirty seconds to disperse the buprenorphine HCl in the Intralipid. The vial was stirred at a high speed or at about 1000 rpm on a magnetic stirrer at room temperature for two hours or more. Once the buprenorphine has all dissolved, 0.18 ml of 0.1 N NaOH (sterile filtered) was injected into the vial containing 7.5 mg buprenorphine and Intralipid®. The vial was stirred at a high speed or at about 1000 rpm on a magnetic stirrer at room temperature for two hours or more prior to administration.

Preparation of 0.8 Mg/Ml of Buprenorphine Aqueous Suspension at pH 6.8

A solution of 1% PVP K-30 and 1.4% glycerin was prepared. For example, 2.5 g PVP and 3.5 g glycerin were added to a 250 ml volumetric flask and q.s with water. 4.5 mg of buprenorphine HCl was accurately weighed in a vial and 5 mL of the PVP and glycerin solution was added. The solution was stirred until dissolved. Sterile filtering of the solution then occurred. 0.05 ml of sterile 0.1 N NaOH was added to the vial containing 0.8 mg/ml of buprenorphine (free base equivalent) while the vial was stirring on a magnetic stirrer. The vial was stirred at 1000 rpm (fast setting) on the magnetic stirrer at room temperature for three hours prior to administration.

In Vitro Release Studies
Buprenorphine HCl Emulsion Preparation

Buprenorphine HCl (~2.4 mg) was weighed, dissolved in 3 mL of 5%, 10% or 20% Intralipid emulsion to reach a final concentration of ~0.5 mg/mL. The pH of buprenorphine emulsions were ~5.0 without pH adjustment. The pH was adjusted to about pH 8.0 with dilute NaOH. Both emulsions with different pHs were evaluated for their release characteristics.

Buprenorphine HCl Suspension Preparation

Buprenorphine HCl (~11 mg) was weighed, dissolved in distilled water and made up to 10 mL, in a volumetric flask to reach a final concentration of ~1.1 mg/mL. A 3 mL aliquot of this solution was used to prepare a suspension by adjusting the solution to various pH values (6.6, 6.8, 7.0) by adding dilute NaOH. A portion of the buprenorphine HCl was precipitated as the free base and the remaining portion was dissolved as the hydrochloride salt form.

Release Studies

A dialysis tubing with a length of 5 to 10 cm (Spectrum, 4 mm diameter, 8,000 MWCO) was used to hold emulsion, suspension or solution formulations containing buprenorphine. The tubing was first wetted in distilled water and the appropriate amount of formulations (~0.5 mL) was introduced into the tubing with a syringe. The dialysis tubing was then sealed with plastic clamps to prevent leakage and was placed into 20 mL of release medium in a covered Petri dish. The release solution was stirred magnetically. At appropriate time intervals, 5 mL samples were withdrawn and replaced with fresh medium. The release samples were analyzed for buprenorphine by HPLC.

HPLC Analysis

The mobile phase was prepared as described in USP 24 (p. 258). Ammonium acetate (1 g) was dissolved in 100 mL of distilled water to obtain a 1% solution. To this solution, a 100 µL aliquot of glacial acetic acid was added and this buffer was then added to 600 mL of HPLC grade methanol and the solution was filtered through a 0.22 µm filter and de-gassed. The mobile phase flow rate was 1 mL/min with an injection volume of 100 µL. The detection wavelength was either 250 nm or 288 nm.

The HPLC system was a Shimadzu system including a LC-10AT pump, SIL-10AD auto injector, SPD-10A UV-Visible detector, and SCL-10A system controller with Shimadzu Class VP software (ver. 4.3) for system control and data acquisition. The column was a Waters SymmetryShield™ RP18, 5 µm particle size, 3.9*100 mm, with a C18 guard column.

Release Studies from Intralipid Emulsions Using Dialysis Tubing

Buprenorphine release data from Intralipid emulsions at different pH values are tabulated in Table 1 and plotted in FIG. 1.

TABLE 1

| | Buprenorphine release profile from Intralipid emulsions into NS. | | | | | |
|---|---|---|---|---|---|---|
| | % Released | | | | | |
| Time (hr) | 5% Intralipid pH 5.02 | 10% Intralipid pH 5.30 | 20% Intralipid pH 5.79 | 5% Intralipid pH 7.92 | 10% Intralipid pH 8.06 | 20% Intralipid pH 7.81 |
| 0.5 | 15.7 | 8.5 | 5.1 | 3.4 | 2.5 | 2.8 |
| 1 | 25.7 | 15.8 | 8.5 | 4.9 | 4.1 | 3.7 |
| 2 | 35.3 | 23.0 | 15.3 | 7.9 | 7.1 | 4.7 |
| 4 | 46.7 | 34.0 | 22.7 | 13.4 | 10.7 | 6.9 |
| 6 | 48.5 | 35.7 | 30.8 | 20.6 | 14.6 | 10.6 |

TABLE 1-continued

Buprenorphine release profile from Intralipid emulsions into NS.

| | % Released | | | | | |
|---|---|---|---|---|---|---|
| Time (hr) | 5% Intralipid pH 5.02 | 10% Intralipid pH 5.30 | 20% Intralipid pH 5.79 | 5% Intralipid pH 7.92 | 10% Intralipid pH 8.06 | 20% Intralipid pH 7.81 |
| 8 | — | — | — | 23.8 | 19.7 | 11.3 |
| 11 | 56.3 | 43.0 | 40.0 | — | — | — |
| 24 | 54.2 | 43.0 | 46.6 | 43.1 | 42.0 | 34.7 |

Release Studies from Various pH Suspensions Using Dialysis Tubing

Figure 2:
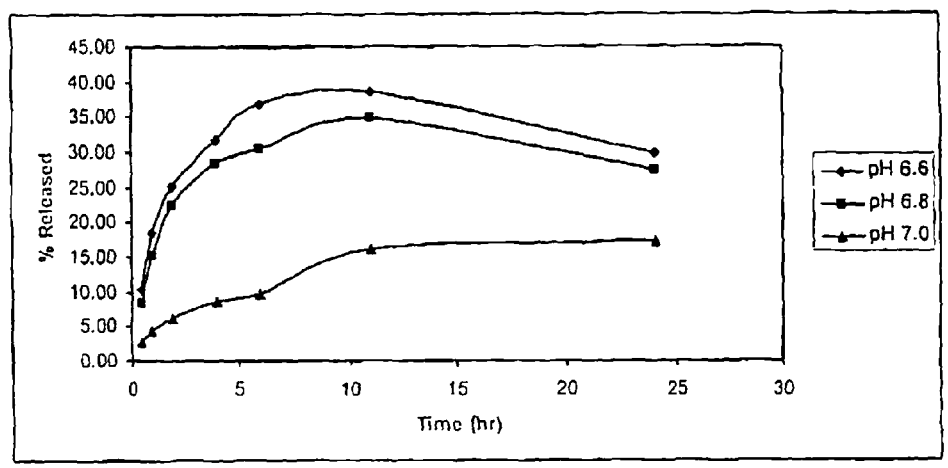
FIG. 2 is a chart demonstrating buprenorphine release profile from suspensions at various pH values into NS.

Buprenorphine release data from suspensions with different pH values are tabulated in Table 2 and plotted in FIG. 2.

TABLE 2

Buprenorphine release profile from suspension with various pH values into NS

| | % Released | | |
|---|---|---|---|
| Time (hr) | pH 6.6 | pH 6.8 | pH 7.0 |
| 0.5 | 10.4 | 8.4 | 2.8 |
| 1 | 18.5 | 15.2 | 4.4 |
| 2 | 25.2 | 22.6 | 6.1 |
| 4 | 31.7 | 28.5 | 8.5 |
| 6 | 36.9 | 30.5 | 9.7 |
| 11 | 38.7 | 34.9 | 16.2 |
| 24 | 29.7 | 27.4 | 17.2 |

Example Two

In Vivo Subcutaneous Administration of Emulsion and Suspension Formulations in Rats Buprenorphine HCl Solution Preparation Buprenorphine HCl (~4.3 mg) was weighed, dissolved in distilled water and made up to 5 mL in a volumetric flask to reach a final concentration of ~0.8 mg/mL buprenorphine free base equivalent.

Buprenorphine HCl Emulsion Preparation

Buprenorphine HCl (~2.58 mg) was weighed, dissolved in 3 mL of 5%, 10% or 20%

Intralipid emulsion to reach a final concentration of ~0.8 mg/mL buprenorphine free base equivalent. The pH was adjusted to ~8.0 with 0.1N NaOH.

Buprenorphine HCl Suspension Preparation

Polyvinylpyrrolidone (~0.25 g, PVP K-30) was weighed, dissolved in water and made up to 25 mL in a volumetric flask to reach a final concentration of 1%. Buprenorphine HCl (~8.61 mg) was weighed and dissolved in 10 mL of 1% PVP solution to reach a final concentration of ~0.8 mg/mL buprenorphine free base equivalent. An aliquot (3 mL) of this solution was used to prepare the suspension in 1% PVP by raising the pH to 6.8 using 0.1N NaOH.

In Vivo Studies

Three, 250-300 g, male Sprague-Dawley rats were tested for each formulation. Animals were obtained from the vendor on a weekly basis, and each group of animals was allowed to acclimate to the housing facility for at least 24 hours. Animals were allowed full access to food and water before and during the experiment, and each animal was weighed prior to formulation administration (Table 3).

A 0.3 mL, 29 gauge insulin syringe was filled with formulation (50 µl) using aseptic technique. The skin at the nape of the rat's neck was lifted and the needle was inserted under the skin, parallel to the long axis of the skin fold. Approximately 2-3 min prior to each sampling time, the animal was placed into a plexiglass rat restrainer (Harvard Bioscience, Holliston, Mass.), keeping the tail free. To dilate the tail vein for sampling, the tail was placed briefly (~10 sec) into warm water (70-80° C.) and was then kept warm by placing it ~1 cm beneath a 100 W light bulb for one minute. Precautions were taken to ensure that the animal was not burned during these procedures. Blood was collected from the tail vein using a heparinized, 23G butterfly needle. The tubing from the butterfly needle was trimmed to ~1 cm from the hub to reduce the dead volume. Approximately 8-10 drops of blood were collected into 1.5 ml polypropylene centrifuge tube that had been previously rinsed with heparinized EIA buffer (see below). From this sample, 50 µl of whole blood was transferred to another vial containing 200 µl of heparinized (10,000 U/L) EIA buffer (1:5 dilution). Both the remaining whole blood and diluted blood samples were immediately frozen using a dry ice/acetone bath and then stored at −70° C. until analysis.

ELISA Analysis:

Buprenorphine ELISA kits were obtained from Neogen Corp (Lexington, Ky.) and used as directed. Briefly, 20 µl of sample (1:5 dilution of whole blood, calibration standard, or Neogen-supplied control in EIA buffer) was pipetted into the well of a 96 well plate. Drug-enzyme (horseradish peroxidase) conjugate (180× dilution in EIA buffer) was placed into each well, the cover supplied was placed on top of the plate and the system was shaken for 45 min at ambient temperature on a microplate shaker (Precision Scientific, Chicago, Ill.). The liquid was removed from the plate by inversion, and 300 µl of wash buffer (1:10 dilution in EIA buffer) was added into each well. The plate was inverted to remove the buffer and the washing step was repeated two additional times. Following the removal of the final wash buffer, 150 µl of K-Blue substrate (3',3',5,5' tetramethylbenzidine; hydrogen peroxide) was added to each well and the system was placed on a microplate shaker at ambient temperature for thirty minutes. Red Stop Solution (50 µl) was added to each well, the plate was gently mixed and the absorbance read at 650 nm (Molecular Devices, Model 384, Union City, Calif.). Calibration standards were prepared using buprenorphine HCl (Diosynth, lot # L00025491). A calibration curve was prepared for each experiment/plate by plotting the optical density readings versus buprenorphine concentrations from the standards included on the plate. A calibration curve was established with these results using regression analysis. The limit of quantitation used for all assays was 0.8 ng/mL.

Bioavailability comparisons between formulations can be made using the area under the plasma concentration-time curve. The AUC was calculated by summing the areas of any two adjacent time points by trapezoidal rule. No extrapolation beyond the final collection time was made.

Figure 3:
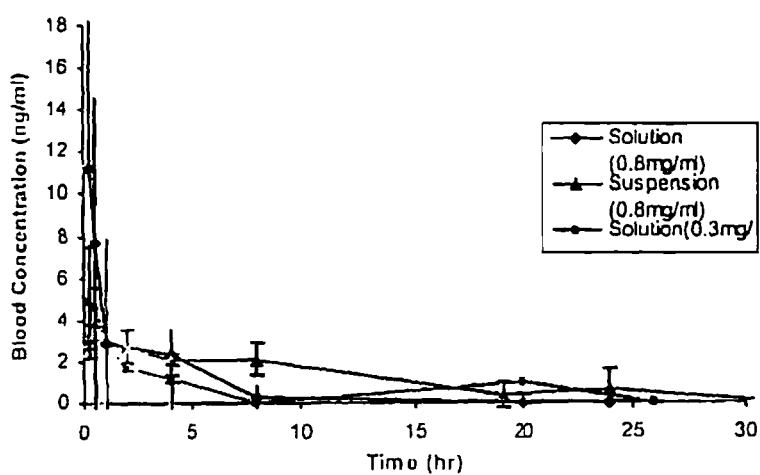
FIG. 3 is a chart of a buprenorphine blood concentration-time profile after subcutaneous administration of solution and suspension formulations in rats.
Figure 4:
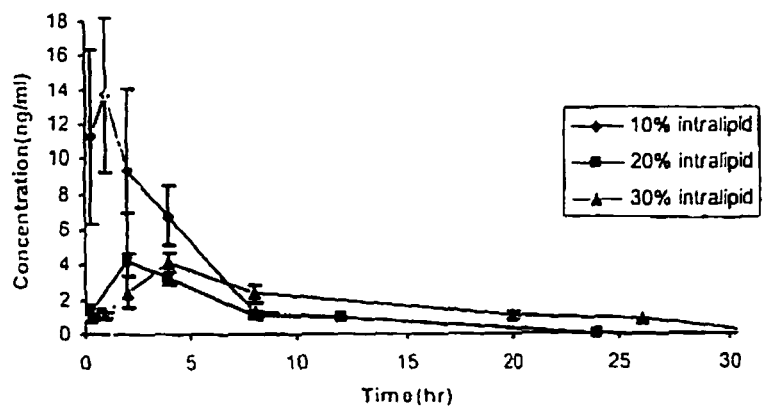
FIG. 4 is a chart of a buprenorphine blood concentration-time profile after subcutaneous administration of emulsions containing 0.8 mg/ml of buprenorphine with various concentrations of Intralipid® in rats.

Results:

The blood concentration-time profiles following subcutaneous administration of long-acting buprenorphine formulations are shown in FIGS. 3 and 4. The pharmacokinetic parameters ($C_{max}$, $t_{max}$, AUC) derived from the mean (N.D.=0) concentration-time profiles are listed in Table 4.

Two different doses of buprenorphine were administered as solutions, 15 µg (as 0.3 mg/mL) and 40 µg (as 0.8 mg/mL). As expected, the absorption from the solution formulation (FIG. 3) was rapid, with a $t_{max}$ of ~15 min. The $C_{max}$ values for each were nearly dose-proportional (2.3-fold compared to an expected 2.7-fold increase in $C_{max}$ for the higher dose, Table 4). Both formulations were cleared rapidly, with the greatest differences in blood concentrations observed in the first hour. Buprenorphine could not be detected in the blood after ~8 hours for either dose. The AUC values were not dose-proportional, however, and the low AUC measured for the 40 µg dose may be reflective of the limit of quantitation used for the assay.

The suspension (0.8 mg/ml) gave lower but more prolonged concentrations of buprenorphine in the blood (FIG. 3). Measurable buprenorphine concentrations were detected for up to 56 hours in two of the rats tested. The $t_{max}$ for the suspension occurred at the first sampling time (15 min), and the blood concentration (3.2 ng/mL) at this time was similar to the concentration measured at 56 hours (1.25 ng/ml) (Table 4), indicating that the suspension provided a low, but sustained release of buprenorphine for at least two days.

Significant differences were seen in the performance of the emulsion formulations with varying concentrations of Intralipid® (FIG. 4). The lowest Intralipid® concentration (10%) gave similar results as the solution formulation while the 20% and 30% Intralipid concentrations both showed lower, more prolonged buprenorphine concentrations. As with the solution formulation, measurable levels of buprenorphine were not detected after 8 hours for the 10% Intralipid emulsion. At least one animal had a detectable concentration of buprenorphine at 12 hours with the 20% Intralipid® formulation, and one animal had detectable levels for up to 26 hours with the 30% Intralipid® formulation. The $t_{max}$ was longer (4 hr) for the 30% Intralipid® formulation as compared to the 10% and 20% concentrations (1 hr and 2 hr, respectively). The AUC for the 30% Intralipid® formulation was 1.8-fold greater than with the 20% formulation, while the 10% formulation had the largest AUC due to the extremely high buprenorphine plasma concentrations measured during the first four hours following administration. Based on these data, it appears that the 30% Intralipid® formulation has slightly better sustained action than the other formulations tested.

TABLE 3

Weight of each animal prior to dosing

| Group | Rat 1 Weight (g) | Rat 2 Weight (g) | Rat 3 Weight (g) |
|---|---|---|---|
| Solution (0.3 mg/ml) | 320 | 330 | 322 |
| Solution (0.8 mg/ml) | 325 | 321 | 301 |
| Emulsion (10% Intralipid) | 328 | 330 | 329 |
| Emulsion (20% Intralipid) | 338 | 354 | 353 |
| Emulsion (30% Intralipid) | 360 | 356 | 355 |
| Suspension (0.8 mg/ml) | 320 | 310 | 309 |

TABLE 4

Pharmacokinetic parameters calculated from the blood concentration-time profiles of subcutaneously administered buprenorphine HCl formulations.

| Formulation | $C_{max}$ (ng/ml) | $T_{max}$ (hr) | AUC (hr · ng/ml) |
|---|---|---|---|
| Solution (0.3 mg/ml) | 4.87 | 0.25 | 13.64 |
| Solution (0.8 mg/ml) | 11.23 | 0.25 | 19.92 |
| Emulsion (10% Intralipid) | 13.77 | 1 | 59.60 |
| Emulsion (20% Intralipid) | 4.3 | 2 | 25.39 |
| Emulsion (30% Intralipid) | 4.12 | 4 | 44.86 |
| Suspension (0.8 mg/ml) | 3.2 | 0.25 | 52.29 |

It is understood that the foregoing detailed description and accompanying examples are merely illustrative and are not to be taken as limitations upon the scope of the invention, which is defined solely by the appended claims and their equivalents.

We claim:

1. An oil- and pH-controlled buprenorphine-release formulation consisting of buprenorphine; a pH adjusting agent; and a surfactant that emulsifies said buprenorphine in oil, wherein the pH adjusting agent is NaOH, wherein the concentration of oil is from about 5% to about 20% and the pH of the formulation is from about 5.02 to about 8.06.

2. The formulation according to claim 1 wherein said buprenorphine is selected from the group consisting of a free base and a salt.

3. The formulation according to claim 1, wherein said surfactant is selected from the group consisting of synthetic non-ionic surfactants, polypropylene polyethylene block copolymers, phosphatides, egg phosphatide, polysorbates, other surfactants acceptable for parenteral administration, and combinations thereof.

4. The formulation according to claim 1, wherein said buprenorphine is dissolved in a water immiscible solvent selected from the group consisting of vegetable oil, soybean oil, safflower oil, cottonseed oil, corn oil, sunflower oil, arachis oil, castor oil, olive oil, ester of a medium or long chain fatty acid such as a mono-, di-, or triglyceride, ethyl oleate, isopropyl myristate, polyoxyl hydrogenated castor oil, and combinations thereof.

5. An oil- and pH-controlled buprenorphine-release formulation consisting of buprenorphine; a pH adjusting agent; glycerol; a buffer further selected from the group consisting of sodium citrate and sodium phosphate, and combinations thereof; preservatives selected from the group consisting of EDTA, benzyl alcohol, methyl paraben, propyl paraben, and combinations thereof; and a surfactant that emulsifies said buprenorphine in oil, wherein the pH adjusting agent is NaOH, wherein the concentration of oil is from about 5% to about 20% and the pH of the formulation is from about 5.02 to about 8.06 correspond to a desired release profile of the formulation.

6. The formulation according to claim 1, wherein said buprenorphine is a free base buprenorphine formed by the addition of an alkali metal salt selected from the group consisting of NaOH to buprenorphine salt.

7. The formulation according to claim 1, wherein said suspending agent is selected from the group consisting of polyvinyl pyrrolidone (PVP), sodium carboxymethylcellulose, and dextran.

8. The formulation according to claim 1, wherein the composition has a pH of from about 6 to about 8.

9. The formulation according to claim 1, wherein said buprenorphine is a free base buprenorphine formed by dispersing said buprenorphine free base into the suspending agent solution and mixing the formulation with a high shear homogenizer.

10. The formulation of claim 1, wherein the combination of the concentration of oil and the pH is selected from the group consisting of 5% oil and pH 5.02; 10% oil and pH 5.30; 20% oil and pH 5.79; 5% oil and pH 7.92; 10% oil and pH 8.06; and 20% oil and pH 7.81.

* * * * *